US008486860B2

(12) United States Patent
Grech

(10) Patent No.: US 8,486,860 B2
(45) Date of Patent: Jul. 16, 2013

(54) METHODS OF PROTECTING CROPS FROM POST HARVEST MICROBIAL DECAY

(75) Inventor: Nigel M Grech, Fresno, CA (US)

(73) Assignee: Plant Protectants, LLC, Visalia, CA (US)

( * ) Notice: Subject to any disclaimer, the term of this patent is extended or adjusted under 35 U.S.C. 154(b) by 262 days.

(21) Appl. No.: 12/397,286

(22) Filed: Mar. 3, 2009

(65) Prior Publication Data
US 2009/0227455 A1  Sep. 10, 2009

Related U.S. Application Data

(60) Provisional application No. 61/034,881, filed on Mar. 7, 2008.

(51) Int. Cl.
*A01N 3/02* (2006.01)
*A01N 63/00* (2006.01)
*A01N 65/00* (2009.01)

(52) U.S. Cl.
USPC ........... 504/114; 504/115; 504/117; 252/397; 252/398; 514/73

(58) Field of Classification Search
USPC ...... 504/114, 115, 117; 252/397, 398; 514/73
See application file for complete search history.

(56) References Cited

U.S. PATENT DOCUMENTS

| 1,704,456 | A | | 3/1929 | Barger |
| 1,900,295 | A | | 3/1933 | Ore McDill |
| 1,943,468 | A | | 1/1934 | Bridgeman et al. |
| 2,379,294 | A | * | 6/1945 | Gooding .................. 514/549 |
| 2,443,795 | A | | 6/1948 | MacRill et al. |
| 2,460,710 | A | | 2/1949 | Nolan et al. |
| 2,489,744 | A | | 11/1949 | Brogden |
| 2,920,996 | A | | 1/1960 | Bluestone |
| 3,139,347 | A | | 6/1964 | Sair et al. |
| 3,189,467 | A | | 6/1965 | Kalmar |
| 3,231,392 | A | | 1/1966 | Sair |
| 3,370,957 | A | | 2/1968 | Wagner et al. |

(Continued)

FOREIGN PATENT DOCUMENTS

| CA | 2644188 | 8/2008 |
| DE | 23 44 887 A1 | 3/1975 |

(Continued)

OTHER PUBLICATIONS

Clua et al. (Increase in forage yield in narrowleaf birdsfoot trefoil in permanent pasture with foliar applied gibberellic acid and phosphorus) Plant Growth Regulation 21; p. 223-228, 1997.

(Continued)

*Primary Examiner* — Jane C Oswecki
(74) *Attorney, Agent, or Firm* — Mark D. Miller

(57) ABSTRACT

Methods for protecting fruit, vegetables and ornamentals against post harvest microbial decay by applying systemic acquired resistance inducers in combination with sorbic acid, and/or one or more of its alkali metal salts, and/or phosphorous acid, and/or one or more of its alkali metal salts.

16 Claims, 9 Drawing Sheets

Uninoculated Control (Treatment A) of Example 1 at Day 4

U.S. PATENT DOCUMENTS

| | | | |
|---|---|---|---|
| 3,410,696 | A | 11/1968 | Rosenfeld |
| 3,420,790 | A | 1/1969 | Gassner et al. |
| 3,658,813 | A | 4/1972 | Godefroi et al. |
| 3,759,719 | A | 9/1973 | Hodel et al. |
| 3,888,984 | A | 6/1975 | Hughes et al. |
| 4,006,259 | A | 2/1977 | Kalmar |
| 4,075,324 | A * | 2/1978 | Thizy et al. |
| 4,434,185 | A | 2/1984 | Nelson |
| 4,614,659 | A | 9/1986 | Liu |
| 4,917,820 | A * | 4/1990 | Matsumoto et al. .......... 252/397 |
| 5,500,403 | A * | 3/1996 | Shafer et al. .................. 504/115 |
| 5,707,418 | A | 1/1998 | Hsu |
| 5,736,164 | A | 4/1998 | Taylor |
| 5,800,837 | A | 9/1998 | Taylor |
| 5,865,870 | A | 2/1999 | Hsu |
| 5,922,649 | A | 7/1999 | Pehu et al. |
| 5,997,910 | A | 12/1999 | Taylor |
| 6,083,876 | A | 7/2000 | Joniken et al. |
| 6,114,285 | A | 9/2000 | Padilla et al. |
| 6,139,879 | A | 10/2000 | Taylor |
| 6,168,643 | B1 | 1/2001 | Hsu |
| 6,228,885 | B1 | 5/2001 | Palla et al. |
| 6,338,860 | B1 | 1/2002 | Taylor |
| 6,509,041 | B2 | 1/2003 | Taylor |
| 8,076,266 | B2 | 12/2011 | Dean |
| 8,101,548 | B2 | 1/2012 | Dean |
| 2003/0087014 | A1* | 5/2003 | Kemp et al. ................... 426/321 |
| 2006/0084573 | A1 | 4/2006 | Grech et al. |
| 2007/0142227 | A1* | 6/2007 | Rajamannan ................. 504/117 |
| 2008/0014306 | A1 | 1/2008 | Castro |
| 2008/0145499 | A1 | 6/2008 | Sardo |
| 2008/0248128 | A1 | 10/2008 | Sardo |
| 2009/0095040 | A1* | 4/2009 | Dean ................................ 71/29 |
| 2009/0227455 | A1 | 9/2009 | Grech |
| 2009/0306210 | A1 | 12/2009 | Behnam |

FOREIGN PATENT DOCUMENTS

| | | |
|---|---|---|
| DE | 197 10 127 A1 | 9/1998 |
| DE | WO 2007 101495 | 9/2007 |
| EP | 336489 | 10/1989 |
| EP | 1941802 | 6/2008 |
| ES | 2078180 | 12/1995 |
| ES | 2303808 | 8/2008 |
| JP | 64 010943 | 1/1989 |
| WO | 99-12422 | 3/1999 |
| WO | 00-16644 | 3/2000 |
| WO | 2003-011030 | 2/2003 |
| WO | 2005-074684 | 8/2005 |
| WO | 2007-017409 | 2/2007 |
| WO | 2007/101495 A | 9/2007 |
| WO | 2007-101848 | 9/2007 |
| WO | 2007-128743 | 11/2007 |
| WO | 2008000741 | 1/2008 |
| WO | 2008-034785 | 3/2008 |

OTHER PUBLICATIONS

Brown, G.E., Plant Disease, vol. 68, No. 5, pp. 415-417. 1984.
Aharoni, Y., et al., New Zealand Journal of Crop and Horticultural Science, vol. 20, No. 2, pp. 177-179. 1992.
Chastagner, et al., Phytopathology (USA), Jan. 1979.
Smilanick, et al., Plant Disease, Am. Phytopath. Society, 1997.
Sugar, et al., Management of Nitrogen and Calcium in Pear Trees for Enhancement of Fruit Resistance to Postharvest Decay; Hort-Technology, vol. 2(3), Jul.-Sep. 1992, pp. 382-387, Published by American Society for Hortcultural Science, Alexandria, VA.
Wills, R., et al. "Postharvest an Introduction to the Physiology & Handling of Fruit, Vegetables and Ornamentals" University of New South Wales Press Ltd., Chapter 9, pp. 144-158 (4th Ed. 1998).
Igoe, R. "Dictionary of Food Ingredients" Van Nostrand Reinhold, New York, pp. 28-29, 102-103, 108-109, and 128-129 (1989).
Kader, A. "Postharvest Technology of Horticultural Crops" University of California Agriculture and Natural Resources Publication 3311, Chapter 17, pp. 163-195, (Third Ed. 2002).
David Sugar, Timothy L. Righetti, Enrique E. Sanchez, Habibi Khemira; Management of Nitrogen and Calcium in Pear Trees for Enhancement of Fruit Resistance to Postharvest Decay; Hort-Technology, vol. 2(3), Jul.-Sep. 1992, pp. 382-387; Published by American Society for Horticultural Science, Alexandria, VA 22314.
Journal of Bacteriology, Influence of Sorbic Acid on the Growth of Certain Species of Bacteria, Yeasts, and Filamentous Fungi, 771 pp. 573-580, 1959, Bell, et al.
Food Technology, vol. 59, No. 2, pp. 124-128.
The Commercial Storage of Fruits, Vegetables, and Florist and Nursery Stocks, USDA Handbook No. 66, Sep. 1954, Wright, et al.
John N. Sofos: "Interactions and Synergistic Effects"; Sorbate Food Preservatives, Jan. 1, 1989, pp. 55-94, XP009120020, ISGN: 0-8493-6786-7 (p. 72 paragraphs 2 through 5 and p. 75, paragraphs 2 through 5).
Tomlin C D S: "661 Phosphonic acid", The E-Pesticide Manual, a World Compendium, Jul. 2006 (Jul. 2007), XP002537979, ISGN: 1 901396 42 8; Section "Products".
Garcia-Luis A; Agusti M; Almela V: Romero E; Guardiola J L: Effect of gibberellic acid on ripening and peel puffing in satsuma mandarin, Scientia Horticulturae, vol. 27, 1985 pp. 75-86 (ISSN 0304-4238).
Gross J; Bazak H; Blumenfeld A; Ben-Arie R: "Changes in chlorophyll and carotenoid pigments in the peel of triump persimmon (diospyros kaki I.) induce by pre-harvest gibberellin (GA3) treatment" Scientia Horticulturae, vol. 24, 1984 pp. 305- 314, (ISSN 0304-4238).
European Search Report: EP 10 25 0514, Sep. 13, 2010.
European Search Report: EP 09 25 0620, Aug. 7, 2009.
Tomlin, C (Ed): "The E-Pesticide Manual 1999-2000, Gibberellic Acid (379) The Bio Pesticide Manual: 1:07 Plant Growth Regulator" Electronic Pesticide Manual, British Crop Protection Council, GB No. 379, Jan. 1, 1999, pp. 1-2.

* cited by examiner

Uninoculated Control (Treatment A) of Example 1 at Day 4

Inoculated Control (Treatment B) of Example 1 with Blue and Green Mold at Day 4.

Inoculated Control (Treatment B) of Example 1 with Blue and Green Mold at Day 7

Treatment F of Example 1 (2% + 2%) at Day 7

Treatment B, Inoculated Control (Sour Rot) of Example 4 at Day 5

Left: Treatment F of Example 7 at Day 5. Right: Untreated Example 7 at Day 5.
Note flower head drooping, leaf and flower petal flaccidity in the untreated (right).

Left: Untreated Example 7 at Day 7. Right: Treatment F of Example 7 at Day 7.
Note flower head drooping, leaf and flower petal flaccidity in the untreated (left).

Effect of Various Treatments (A-F) on Sour Rot of Tomatoes from Example 5

Effect of Various Treatments (A-E) on Sour Rot of Lemons from Example 4.
The arrow indicates the diameter of the lesion.

METHODS OF PROTECTING CROPS FROM POST HARVEST MICROBIAL DECAY

This application claims the benefit of U.S. Provisional application No. 61/034,881 filed on Mar. 7, 2008, which is incorporated herein by this reference in its entirety.

BACKGROUND OF THE INVENTION

The present invention relates to protecting fruit, vegetables and ornamentals against attack by decay-causing organisms such as fungi. In particular, the present invention relates to methods of protecting fruit or vegetables or ornamentals against post harvest microbial spoilage by applying mixtures of systemic resistance inducers in combination with sorbic acid and/or its alkali metal salts.

FIELD OF THE INVENTION

It is a well-known practice in fruit, vegetable and ornamental processing to apply anti microbial agents to the surface of freshly harvested fruit, vegetables of and ornamentals for the purpose of controlling decay-causing organisms.

Systemic resistance inducers are known to elicit microbial resistance in plants but are not used in post harvest applications in fruit, vegetables and ornamentals because they do not provide control of microorganisms at an acceptable level.

Sorbates are known to impart some degree of protection against microbial decomposition in fruit, vegetables and ornamentals but not at an acceptable commercial level when applied alone.

With increasing regulatory and environmental pressure being applied on the post harvest fruit and vegetable sectors, many antimicrobial materials are being withdrawn or not reregistered. It is therefore desirable to provide methods of protecting fruit or vegetables or ornamentals against post harvest microbial spoilage using materials that are readily available, of low toxicity and not likely to be banned from registration.

The present invention provides for a novel method of reducing microbial spoilage of fruit, vegetables and ornamentals utilizing materials that are of very low mammalian toxicity and are environmentally benign.

SUMMARY OF THE INVENTION

The present invention includes methods for protecting fruit, vegetables and/or ornamentals against post harvest microbial decay by applying systemic resistance inducers in combination with sorbic acid and/or its alkali metal salts. In some embodiments the materials applied to the fruit and/or vegetables include sorbic acid and/or its alkali metal salts as well as phosphorous acid and/or its alkali metal salts and/or ammoniacal salts. It has been determined that sorbic acid and/or its salts alone help protect fruits and vegetables from post harvest decay. It has also been determined that phosphorous acid and/or its salts alone also help protect fruits and vegetables from post harvest decay.

The effect of combinations of sorbic acid (and/or its salts) with phosphorous acid (and/or its salts) in the reduction of post harvest spoilage was found to be greater than the sum of the individual effects of sorbic acid (and/or its salts) alone or phosphorous acid (and/or its salts) alone in reducing post harvest spoilage at low or high temperatures.

DETAILED DESCRIPTION

Figure 1:
FIG. 1 is a photograph of an uninoculated control (treatment A) of navel oranges of example 1 at day 4.
Figure 2:
FIG. 2 is a photograph of an inoculated control (treatment B) of navel oranges of example 1 at day 4.
Figure 3:
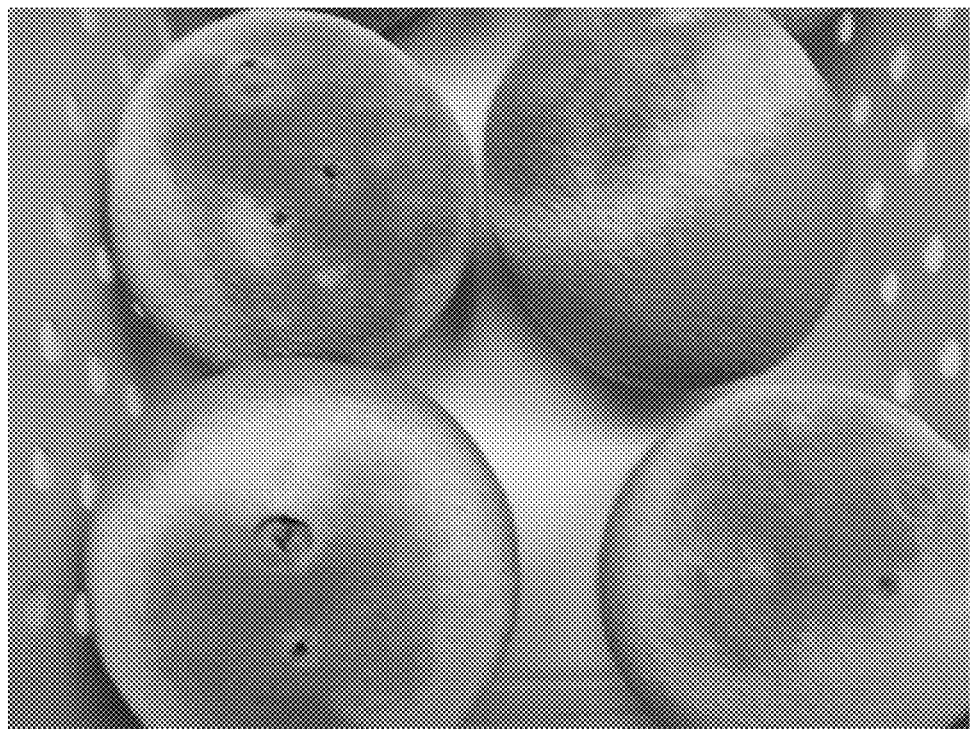
FIG. 3 is a photograph of an inoculated control (treatment B) of navel oranges of example 1 at day 7.
Figure 4:
FIG. 4 is a photograph of navel oranges of treatment F (2%+2%) of example 1 at day 7.
Figure 5:
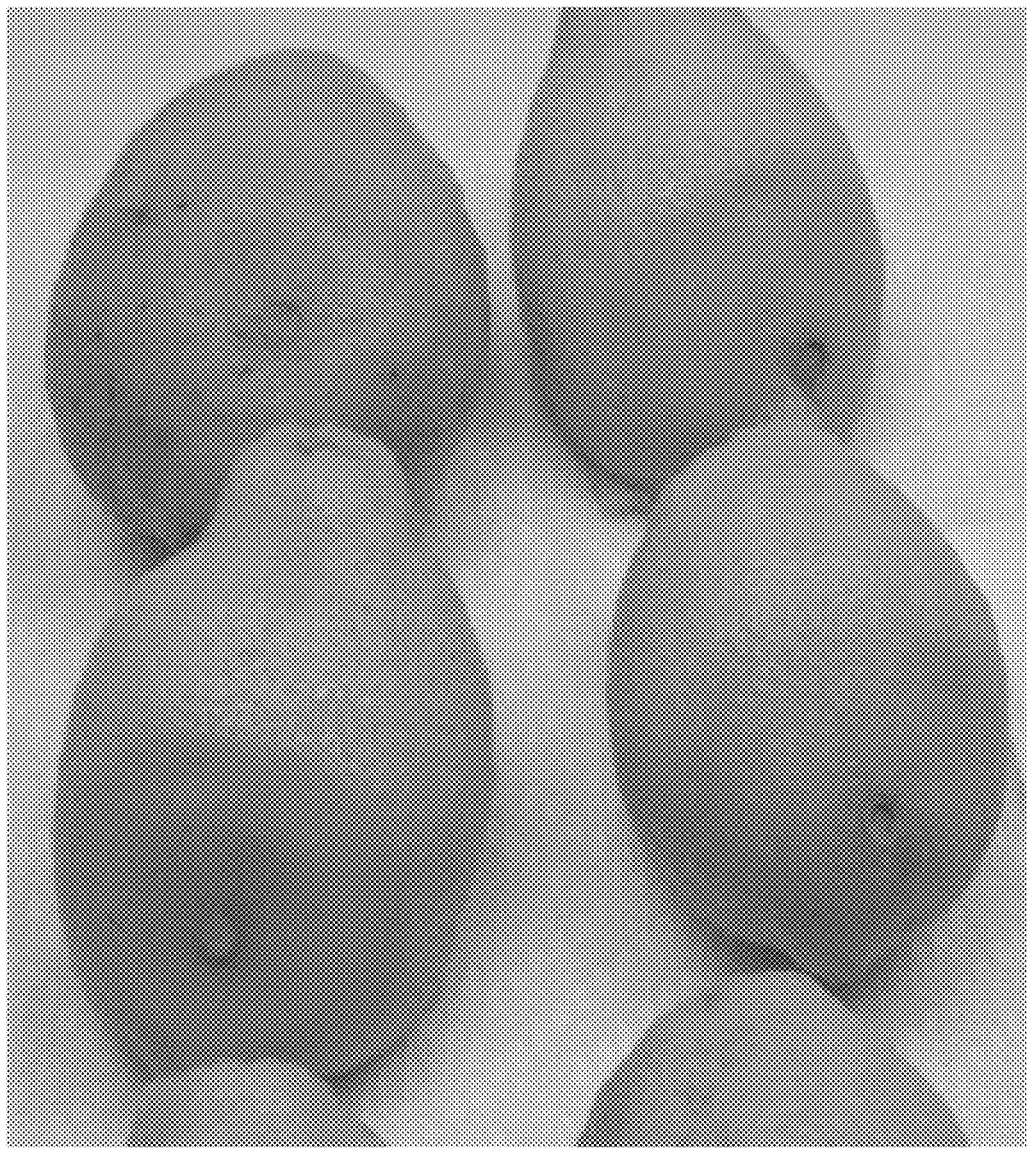
FIG. 5 is a photograph of lemons of the inoculated control (treatment B) of example 4 at day 5.
Figure 6:
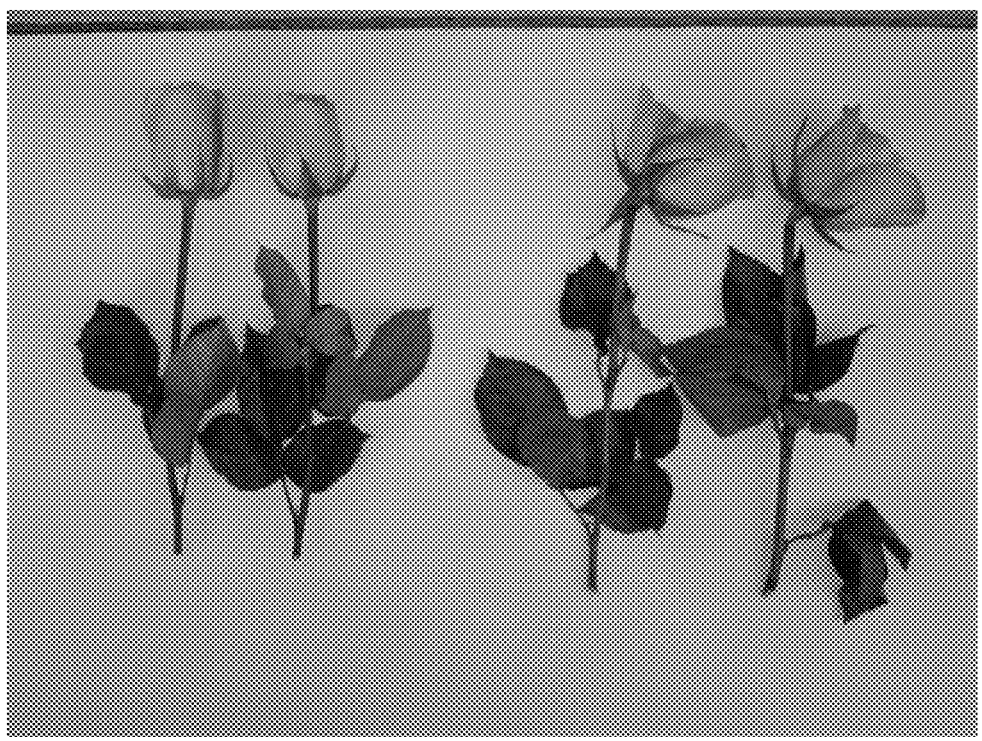
FIG. 6 is a photograph comparing flowers of the untreated control (treatment A) and treatment F of example 7, at day 5.
Figure 7:
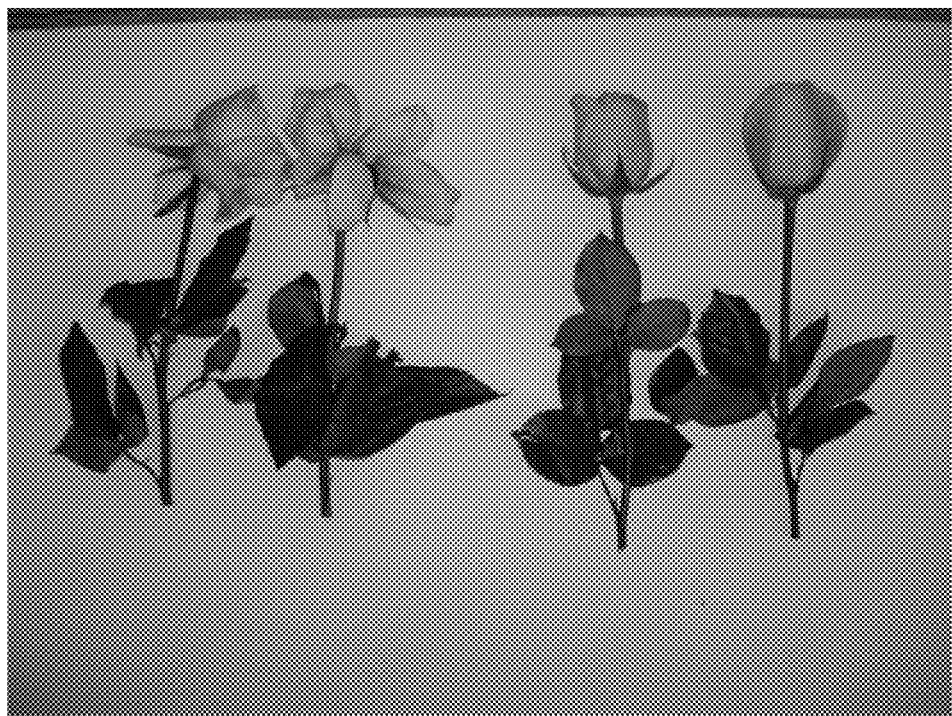
FIG. 7 is a photograph comparing flowers of the untreated control (treatment A) and treatment F of example 7, at day 7.
Figure 8:
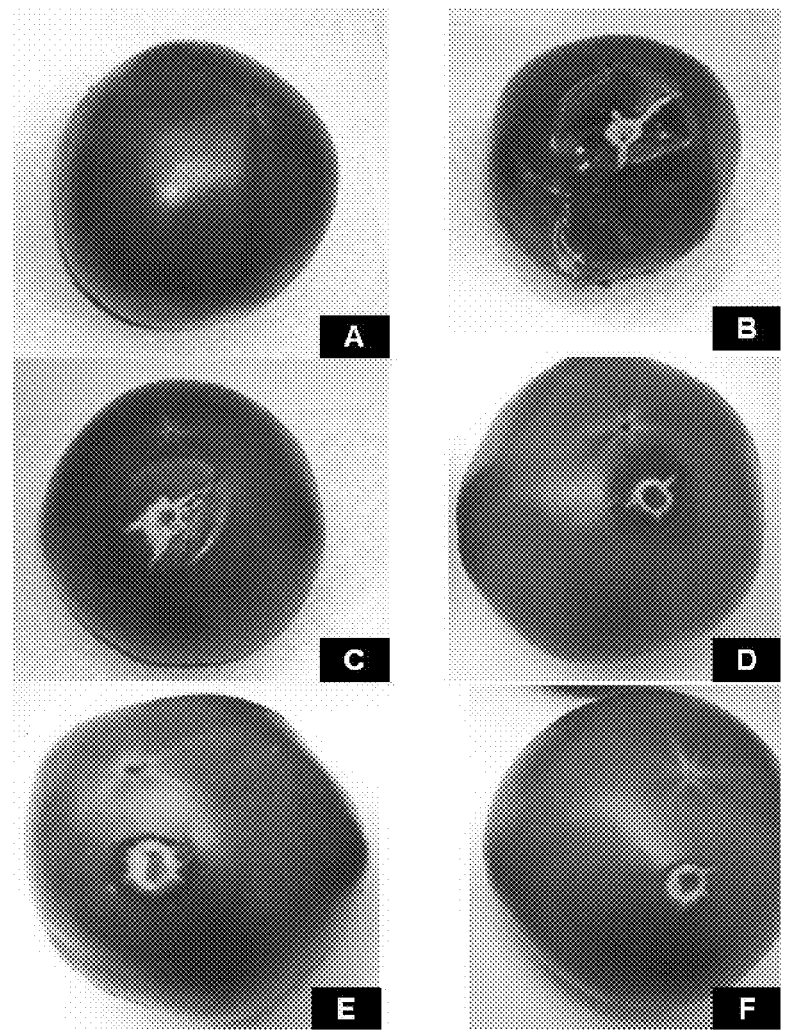
FIG. 8 is a set of photographs showing treatment effects on tomatoes of example 5.
Figure 9:
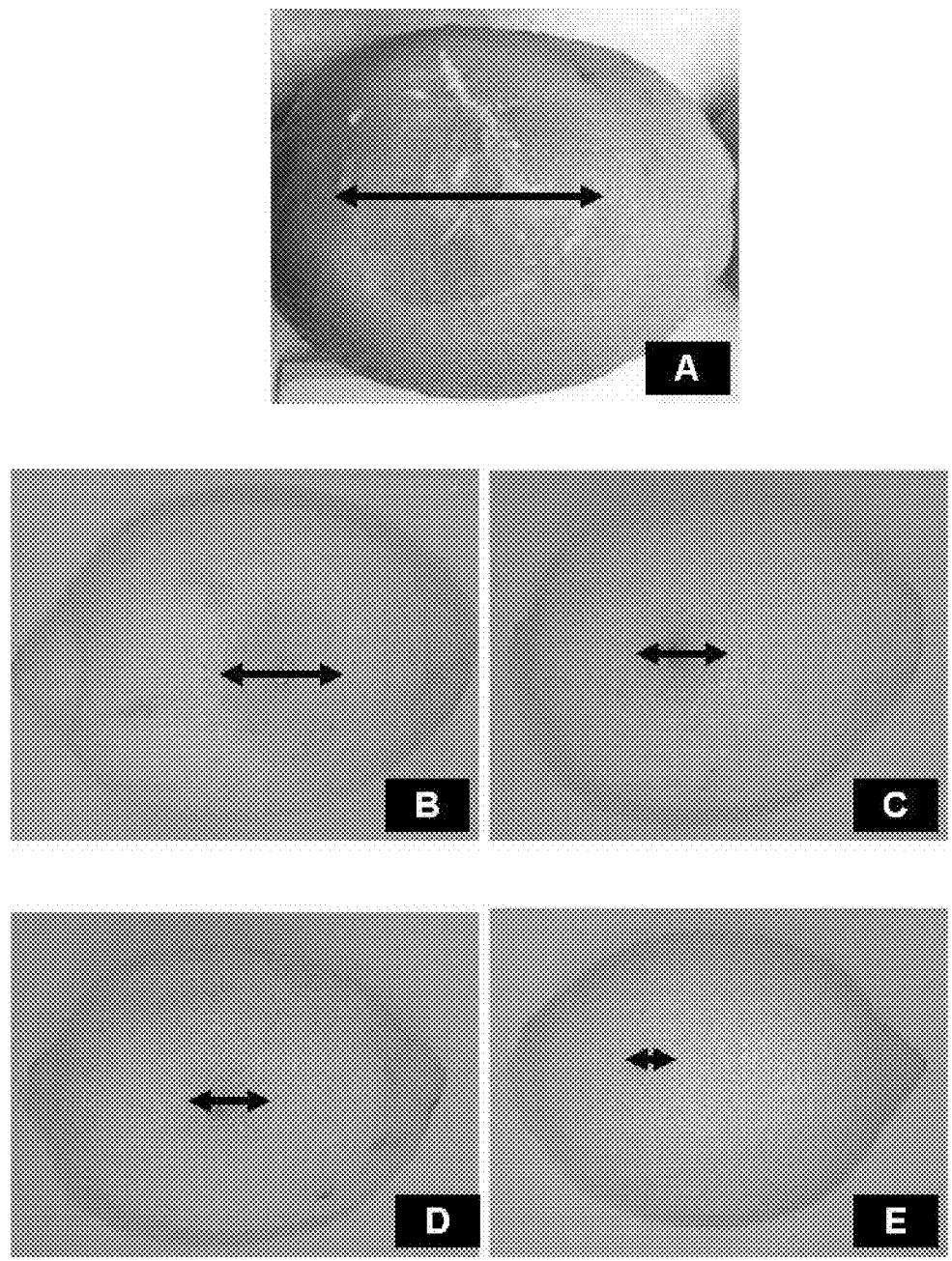
FIG. 9 is a set of photographs showing treatment effects on lemons of example 4.

The invention is further illustrated by the following non-limiting examples.

EXAMPLE 1

In example 1, seven different treatments (A-G below) were made. There were four replications for each of the seven treatments, with each replicate comprising six fruit pieces. Thus, each treatment was applied to 24 fruit pieces. The fruit treated in this example were six fleshly harvested, mature navel oranges. Immersion temperatures were approximately 25° C.

Treatments were as follows:

A. Fruit immersed in water. Untreated uninoculated control.

B. Fruit immersed in water. Untreated inoculated control.

C. Fruit immersed in a solution containing 2% (w/w) potassium sorbate for 2 minutes.

D. Fruit immersed in a solution containing 2% (w/w) potassium phosphite for 2 minutes.

E. Fruit immersed in a solution containing a mixture of 1% (w/w) potassium sorbate and 1% (w/w) potassium phosphite, for 2 minutes.

F. Fruit immersed in a solution containing a mixture of 2% (w/w) potassium sorbate and 2% (w/w) potassium phosphite, for 2 minutes.

G. Fruit immersed in a solution containing a mixture of 3% (w/w) potassium sorbate and 3% (w/w) potassium phosphite, for 2 minutes.

After the treatments were applied and left to dry for 10 minutes, treatments B through G were inoculated with a mixed inocula of Green mold (*P. digitatum*) and Blue mold (*P. italicum*). Fruit inoculation was performed by piercing the fruit skin to a depth of 3-5 mm with a needle coated with spores from both fungi. Fruit was incubated at approximately 25° C. and decay development measured over 7 days from inoculation.

This experiment was repeated twice.

Results of Example 1:

TABLE 1

| | (Mean of two experiments) | |
| --- | --- | --- |
| Treatment | Lesion diameter (mm) day 7 | % change from inoculated control |
| A | 0 | — |
| B | 33 | — |
| C | 16 | −51 |
| D | 12 | −63 |
| E | 8 | −25 |

TABLE 1-continued (Mean of two experiments)

| Treatment | Lesion diameter (mm) day 7 | % change from inoculated control |
|---|---|---|
| F | 12 | −63 |
| G | 4 | −87 |

EXAMPLE 2

In example 2, seven different treatments (A-G below) were made. There were four replications for each of the seven treatments, with each replicate comprising six fruit pieces. Thus, each treatment was applied to 24 fruit pieces. The fruit treated in this example were six freshly harvested, mature lemons. Immersion temperatures were approximately 25° C.

Treatments were as follows:

A. Fruit immersed in water. Untreated uninoculated control.

B. Fruit immersed in water. Untreated inoculated control.

C. Fruit immersed in a solution containing 2% (w/w) potassium sorbate for 2 minutes.

D. Fruit immersed in a solution containing 2% (w/w) potassium phosphite for 2 minutes.

E. Fruit immersed in a solution containing a mixture of 1% (w/w) potassium sorbate and 1% (w/w) potassium phosphite, for 2 minutes.

F. Fruit immersed in a solution containing a mixture of 2% (w/w) potassium sorbate and 2% (w/w) potassium phosphite, for 2 minutes.

G. Fruit immersed in a solution containing a mixture of 3% (w/w) potassium sorbate and 3% (w/w) potassium phosphite, for 2 minutes.

After the treatments were applied and left to dry for 10 minutes, treatments B through G were inoculated with a mixed inocula of Green mold (*P. digitatum*) and Blue mold (*P. italicum*). Fruit inoculation was performed by piercing the fruit skin to a depth of 3-5 mm with a needle coated with spores from both fungi. Fruit was incubated at approximately 25° C. and decay development measured over 7 days from inoculation.

This experiment was repeated twice.

Results of Example 2:

TABLE 2

(Mean of two experiments)

| Treatment | Lesion diameter (mm) day 7 | % change from inoculated control |
|---|---|---|
| A | 0 | — |
| B | 47 | — |
| C | 28 | −40 |
| D | 24 | −48 |
| E | 9 | −81 |
| F | 11 | −78 |
| G | 7 | −89 |

EXAMPLE 3

In example 3, seven different treatments (A-G below) were made. There were four replications for each of the seven treatments, with each replicate comprising six fruit pieces. Thus, each treatment was applied to 24 fruit pieces. The fruit treated in this example were six freshly harvested, mature navel oranges. Immersion temperatures were approximately 25° C.

Treatments were as follows:

A. Fruit immersed in water. Untreated uninoculated control.

B. Fruit immersed in water. Untreated inoculated control.

C. Fruit immersed in a solution containing 2% (w/w) potassium sorbate for 2 minutes.

D. Fruit immersed in a solution containing 2% (w/w) potassium phosphite for 2 minutes.

E. Fruit immersed in a solution containing a mixture of 1% (w/w) potassium sorbate and 1% (w/w) potassium phosphite, for 2 minutes.

F. Fruit immersed in a solution containing a mixture of 2% (w/w) potassium sorbate and 2% (w/w) potassium phosphite, for 2 minutes.

G. Fruit immersed in a solution containing a mixture of 3% (w/w) potassium sorbate and 3% (w/w) potassium phosphite, for 2 minutes.

After the treatments were applied and left to dry for 10 minutes, treatments B through G were inoculated with a 5 mm diameter mycelia plug of *Geotrichium candidum*, the causal agent of sour rot. Fruit inoculation was performed by removing a 5 mm plug of skin, inserting the mycelia plug of *G. candidum* and replacing the fruit plug in the fruit. Fruit was incubated at approximately 25° C. and decay development measured over 7 days from inoculation.

This experiment was repeated twice.

Results of Example 3:

TABLE 3

(Mean of two experiments)

| Treatment | Lesion diameter (mm) day 7 | % change from inoculated control |
|---|---|---|
| A | 0 | — |
| B | 51 | — |
| C | 39 | −24 |
| D | 28 | −45 |
| E | 15 | −70 |
| F | 10 | −80 |
| G | 12 | −77 |

EXAMPLE 4

In example 4, seven different treatments (A-G below) were made There were four replications for each of the seven treatments, with each replicate comprising six fruit pieces. Thus, each treatment was applied to 24 fruit pieces. The fruit treated in this example were six freshly harvested, mature lemons. Immersion temperatures were approximately 25° C.

Treatments were as follows:

A. Fruit immersed in water. Untreated uninoculated control.

B. Fruit immersed in water. Untreated inoculated control.

C. Fruit immersed in a solution containing 2% (w/w) potassium sorbate for 2 minutes.

D. Fruit immersed in a solution containing 2% (w/w) potassium phosphite for 2 minutes.

E. Fruit immersed in a solution containing a mixture of 1% (w/w) potassium sorbate and 1% (w/w) potassium phosphite, for 2 minutes.

F. Fruit immersed in a solution containing a mixture of 2% (w/w) potassium sorbate and 2% (w/w) potassium phosphite, for 2 minutes.

G. Fruit immersed in a solution containing a mixture of 3% (w/w) potassium sorbate and 3% (w/w) potassium phosphite, for 2 minutes.

After the treatments were applied and left to dry for 10 minutes, treatments B through G were inoculated with a 5 mm diameter mycelia plug of *Geotrichium candidum*, the causal agent of sour rot. Fruit inoculation was performed by removing a 5 mm plug of skin, inserting the mycelia plug of *G. candidum* and replacing the fruit plug in the fruit. Fruit was incubated at approximately 25° C. and decay development measured over 7 days from inoculation.

This experiment was repeated twice.

Results of Example 4:

TABLE 4

(Mean of two experiments)

| Treatment | Lesion diameter day 7 | % change from inoculated control |
|---|---|---|
| A | 0 | — |
| B | 68 | — |
| C | 43 | −37 |
| D | 40 | −42 |
| E | 12 | −83 |
| F | 6 | −92 |
| G | 9 | −88 |

EXAMPLE 5

In example 5, seven different treatments (A-G below) were made. There were four replications for each of the seven treatments, with each replicate comprising six fruit pieces. Thus, each treatment was applied to 24 fruit pieces. The fruit treated in this example were six firm but ripe tomatoes. Immersion temperatures were approximately 25° C.

Treatments were as follows:

A. Fruit immersed in water. Untreated uninoculated control.

B. Fruit immersed in water. Untreated inoculated control.

C. Fruit immersed in a solution containing 2% (w/w) potassium sorbate for 2 minutes.

D. Fruit immersed in a solution containing 2% (w/w) potassium phosphite for 2 minutes.

E. Fruit immersed in a solution containing a mixture of 1% (w/w) potassium sorbate and 1% (w/w) potassium phosphite, for 2 minutes.

F. Fruit immersed in a solution containing a mixture of 2% (w/w) potassium sorbate and 2% (w/w) potassium phosphite, for 2 minutes.

G. Fruit immersed in a solution containing a mixture of 3% (w/w) potassium sorbate and 3% (w/w) potassium phosphite, for 2 minutes.

After the treatments were applied and left to dry for 10 minutes, treatments B through G were inoculated with a 5 mm diameter mycelia plug of *Geotrichium candidum* the causal agent of sour rot. Fruit inoculation was performed by removing a 5 mm plug of skin, inserting the mycelia plug of *G. candidum* and replacing the fruit plug in the fruit. Fruit was incubated at 25° C. and decay development measured over 7 days from inoculation. This experiment was repeated twice.

Results of Example 5:

TABLE 5

(Mean of two experiments)

| Treatment | Lesion diameter day 7 | % change from inoculated control |
|---|---|---|
| A | 0 | — |
| B | 68 | — |
| C | 43 | −37 |

TABLE 5-continued (Mean of two experiments)

| Treatment | Lesion diameter day 7 | % change from inoculated control |
|---|---|---|
| D | 40 | −42 |
| E | 12 | −83 |
| F | 6 | −92 |
| G | 9 | −88 |

EXAMPLE 6

In example 6, five different treatments (A-E below) were made. There were four replications for each of the seven treatments, with each replicate comprising six fruit pieces. Thus, each treatment was applied to 24 fruit pieces. The fruit treated in this example were six freshly harvested, mature lemons. Immersion temperatures were approximately 25° C.

Treatments were as follows:

A. Fruit immersed in water at 25° C. Untreated inoculated control.

B. Fruit immersed in a solution containing 2% (w/w) potassium sorbate for 2 minutes.

C. Fruit immersed in a solution containing 2% (w/w) potassium phosphite for 2 minutes.

D. Fruit immersed in a solution containing a mixture of 2% (w/w) potassium sorbate and 2% (w/w) potassium phosphite, for 2 minutes at 25° C.

E. Fruit immersed in a solution containing a mixture of 2% (w/w) potassium sorbate and 2% (w/w) potassium phosphite, for 2 minutes at 50° C.

After the treatments were applied and left to dry for 10 minutes, treatments B through E were inoculated with a 3 mm diameter mycelia plug of *Geotrichium candidum*, the causal agent of sour rot, Fruit inoculation was performed by removing a 3 mm plug of skin, inserting the mycelia plug of *G. candidum* and replacing the fruit plug in the fruit. Fruit was incubated at approximately 25° C. and decay development measured over 7 days from inoculation.

Results of Example 6:

TABLE 6

(Mean of two experiments)

| Treatment | Lesion diameter day 7 | % change from inoculated control |
|---|---|---|
| A | 68 | — |
| B | 31 | −51 |
| C | 24 | −68 |
| D | 11 | −81 |
| E | 3 | −96 |

EXAMPLE 7

In example 7, ten different treatments (A-J below) were made. There were four replications for each of the seven treatments, with each replicate comprising six flowers with associated stems. Thus, each treatment was applied to 24 flower stems. The plants treated in this example were six long stemmed roses in hydrating solutions as listed below. Stems were immersed in the various solutions for a maximum of 10 days. The solutions were occasionally topped up with water over the 10 day period to account for evapo-transpirational losses. Treatment temperatures were approximately 25° C.

Treatments were as follows:

A. Flower stems immersed in water. Untreated control.

B. Flower stems immersed in a solution containing 0.1% (w/w) potassium sorbate

C. Flower stems immersed in a solution containing 0.1% (w/w) potassium phosphite D. Flower stems immersed in a solution containing 0.2% (w/w) potassium sorbate E. Flower stems immersed in a solution containing 0.2% (w/w) potassium phosphite F. Flower stems immersed in a solution containing a mixture of 0.1% (w/w) potassium sorbate and 0.1% (w/w) potassium phosphite.

G. Flower stems immersed in a solution containing a mixture of 0.2% (w/w) potassium sorbate and 0.2% (w/w) potassium phosphite.

H. Flower stems immersed in a solution containing a mixture of 0.3% (w/w) potassium sorbate and 0.3% (w/w) potassium phosphite.

I. Flower stems immersed in a solution containing a mixture of 0.25% (w/w) potassium sorbate and 0.25% (w/w) potassium phosphite, J. Flower stems immersed for one hour in a solution containing a mixture of 0.2% (w/w) potassium sorbate and 0.2% (w/w) potassium phosphite, after which they were removed and placed in water for 10 days.

Results of Example 7:

TABLE 7

Mean Flower Condition Index[a]

| Treatment | DAY 0 | DAY 5 | DAY 10 | % IMPROVEMENT COMPARED TO THE CONTROL (A) AT DAY 10 |
|---|---|---|---|---|
| A | 0.3 | 0.8 | 2.5 | — |
| B | 0.3 | 0.5 | 1.8 | 28 |
| C | 0.3 | 1 | 2.5 | 0 |
| D | 0.3 | 0.7 | 2 | 20 |
| E | 0.3 | 0.5 | 1.9 | 24 |
| F | 0.3 | 0.5 | 1.2 | 52 |
| G | 0.3 | 0.5 | 1.4 | 44 |
| H | 0.3 | 0.3 | 1 | 60 |
| I | 0.3 | 0.6 | 1.3 | 48 |
| J | 0.3 | 0.7 | 1.8 | 28 |

[a]Flowers were scored 0-3 in terms of their condition.
0 = healthy
1 = slight flagging, some petal drop.
2 = more than 25% petal drop, slight wilting of flower head.
3 = drooping, flower petal and leaf flaccidity and wilting of the flower head.

EXAMPLE 8

Commercial fruit coating waxes are used to treat fruit in packing houses. Carnauba wax or any other lower-shine waxes such as wood resin and polyethylene waxes are preferred. In this example, carnauba wax was diluted to use strength according to the manufacturers label and applied to navel oranges by momentary immersion in the wax by hand. There were four replications for each of the four treatments below (A-D), with each replicate comprising six fruit pieces. Thus, each treatment was applied to 24 fruit pieces. The fruit was punctured once as described above, after treatment.

Treatments were as follows:

A. Not waxed. Untreated uninoculated control

B. Fruit momentarily immersed in carnauba wax, untreated uninoculated control.

C. Fruit momentarily immersed in carnauba wax containing a mixture of 2% (w/w) potassium sorbate and 2% (w/w) potassium phosphite.

D. Fruit momentarily immersed in carnauba wax containing a mixture of 4% (w/w) potassium sorbate and 4% (w/w) potassium phosphite.

After treatment, fruit was placed in low temperature storage for 30 days, then removed and assessed for decay.

Results of example 8:

TABLE 8

| Treatment | % decay at 30 days post treatment. | % change from control(A) |
|---|---|---|
| A | 38 | — |
| B | 24 | −37 |
| C | 18 | −53 |
| D | 7.1 | −92 |

Solid forms of the invention may be obtained, for example, by evaporating any of the solutions identified in the examples.

It is to be appreciated that, although the invention has been described in terms of exemplary embodiments, it is not limited thereto. Rather, the appended claims should be construed so as to include other variants and embodiments of the invention which may be made by those skilled in the art without departing from the scope and range of equivalents of the invention.

What is claimed is:

1. A method for protecting one of a fruit, a vegetable or an ornamental against post harvest microbial spoilage comprising the step of directly contacting one of a fruit, a vegetable or an ornamental with an aqueous solution comprising
a sorbic acid source selected from the group of sorbic acid, an alkali metal salt of sorbic acid, and combinations thereof wherein said sorbic acid source is present in said solution in a range of between about 0.1% and about 4% w/w; and
a phosphorous acid source selected from the group of phosphorous acid, an alkali metal salt of phosphorous acid, and combinations thereof wherein said phosphorous acid source is present in said solution in a range of between about 1% and about 3% w/w.

2. The method of claim 1 wherein said sorbic acid source is present in a range of between about 1% and about 3% w/w, and wherein said phosphorous acid source is present in a range of between about 1% and about 3% w/w.

3. The method of claim 1 comprising the additional step of at least partially immersing said fruit, vegetable or ornamental in said solution for a time interval between about 5 seconds and about 60 minutes.

4. The method of claim 2 comprising the additional step of at least partially immersing said fruit, vegetable or ornamental in said solution for a time interval between about 5 seconds and about 60 minutes.

5. The method of claim 1 comprising the additional step of at least partially immersing said fruit, vegetable or ornamental in said solution for a time interval between about 1 minute and about 3 minutes.

6. The method of claim 2 comprising the additional step of at least partially immersing said fruit, vegetable or ornamental in said solution for a time interval between about 1 minute and about 3 minutes.

7. The method of claim 1 wherein the fruit, vegetable or ornamental is drenched with the solution.

8. The method of claims 2 wherein the fruit, vegetable or ornamental is drenched with the solution.

9. The method of claim 1 wherein the fruit, vegetable or ornamental is sprayed with the solution.

10. The method of claim 2 wherein the fruit, vegetable or ornamental is sprayed with the solution.

11. A method of protecting one of a fruit, a vegetable or an ornamental against post harvest microbial spoilage comprising the steps of
    preparing a composition comprising a sorbic acid source selected from the group of sorbic acid, an alkali metal salt of sorbic acid, and combinations thereof wherein said sorbic acid source is present in a range of between about 1% and about 4% w/w; and a phosphorous acid source selected from the group of phosphorous acid, an alkali metal salt of phosphorous acid, and combinations thereof, wherein said phosphorous acid source is present in a range of between about 0.1% and about 4% w/w;
    incorporating the composition into a wax coating; and
    directly applying said coating to one of a fruit, vegetable or ornamental.

12. The method of claim 11 wherein said sorbic acid source is present in a range of between about 1% and about 3% w/w.

13. The method of claim 11 wherein said phosphorous acid source is present in a range of between about 1% and about 4% w/w.

14. The method of claim 11 wherein said phosphorous acid source is present in a range of between about 1% and about 3% w/w.

15. The method of claim 14 wherein said sorbic acid source is present in a range of between about 1% and about 3% w/w.

16. The method of claim 2 wherein cut flower stems are placed in said solution for a time interval of not more than 10 days.

\* \* \* \* \*